United States Patent
Maeda et al.

(10) Patent No.: US 11,877,871 B2
(45) Date of Patent: Jan. 23, 2024

(54) INFECTIOUS DISEASE PREVENTION SUPPORTING DEVICE, METHOD AND PROGRAM

(71) Applicant: NIPPON TELEGRAPH AND TELEPHONE CORPORATION, Tokyo (JP)

(72) Inventors: Atsuhiko Maeda, Musashino (JP); Midori Kodama, Musashino (JP); Motonori Nakamura, Musashino (JP); Ippei Shake, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 75 days.

(21) Appl. No.: 17/255,893

(22) PCT Filed: Jun. 25, 2019

(86) PCT No.: PCT/JP2019/025194
§ 371 (c)(1),
(2) Date: Dec. 23, 2020

(87) PCT Pub. No.: WO2020/004399
PCT Pub. Date: Jan. 2, 2020

(65) Prior Publication Data
US 2021/0259642 A1     Aug. 26, 2021

(30) Foreign Application Priority Data
Jun. 29, 2018  (JP) ................. 2018-124713

(51) Int. Cl.
*G08B 21/02*  (2006.01)
*A61B 5/00*  (2006.01)
(Continued)

(52) U.S. Cl.
CPC ............ *A61B 5/746* (2013.01); *A61B 5/1123* (2013.01); *A61B 5/742* (2013.01); *A61B 5/7405* (2013.01);
(Continued)

(58) Field of Classification Search
CPC ...... A61B 5/746; A61B 5/7405; G16H 40/63; G06F 3/016; G06F 3/16; G08B 21/02; G01P 15/18
See application file for complete search history.

(56) References Cited

U.S. PATENT DOCUMENTS

| 4,965,553 A | * | 10/1990 | DelBiondo, II | ... G08B 21/0453 708/111 |
| 10,790,054 B1 | * | 9/2020 | Vleugels | ............... A61B 5/1114 |

(Continued)

FOREIGN PATENT DOCUMENTS

KR    10-20110080337 A    7/2011

OTHER PUBLICATIONS

Shuzo, M., et al., "Wearable Eating Habit Sensing System Using Internal Body Sound", Journal of Advanced Mechanical Design, systems, and Manufacturing, vol. 4, No. 1, 2010, pp. 158 to 166.
(Continued)

*Primary Examiner* — Benyam Haile
(74) *Attorney, Agent, or Firm* — Timothy D. MacIntyre (57) ABSTRACT

An infectious disease prevention supporting device according to an embodiment of the present invention is an infectious disease prevention supporting device including a processor. The processor is configured to perform a detection process that detects a motion of a forearm or a wrist by a user, a proximity determination process that determines whether the user's hand is in proximity to a mucosa of the user's face based on the motion detected by the detection process for a predetermined period of time, and a warning
(Continued)

generation process that generates a warning to suppress the proximity of the user's hand to the mucosa when it is determined by the proximity determination process that the user's hand is in proximity to the mucosa.

9 Claims, 9 Drawing Sheets

(51) Int. Cl.
  *G16H 40/63* (2018.01)
  *A61B 5/11* (2006.01)
  *G06F 3/01* (2006.01)
  *G06F 3/16* (2006.01)
  *G01P 15/18* (2013.01)
(52) U.S. Cl.
  CPC ............ *A61B 5/7455* (2013.01); *G06F 3/016* (2013.01); *G06F 3/16* (2013.01); *G08B 21/02* (2013.01); *G16H 40/63* (2018.01); *A61B 2562/0219* (2013.01); *G01P 15/18* (2013.01)

(56) References Cited

U.S. PATENT DOCUMENTS

| | | |
|---|---|---|
| 2004/0027247 A1 | 2/2004 | Pittman |
| 2011/0144453 A1 | 6/2011 | Kovarik et al. |
| 2016/0140830 A1 | 5/2016 | Hathorn |
| 2017/0220772 A1 | 8/2017 | Vleugels et al. |
| 2018/0027908 A1 | 2/2018 | Greenly |

OTHER PUBLICATIONS

International Search Report issued in PCT/JP2019/025194, dated Sep. 24, 2019.

* cited by examiner

INFECTIOUS DISEASE PREVENTION SUPPORTING DEVICE, METHOD AND PROGRAM

CROSS-REFERENCE TO RELATED APPLICATIONS

This is a U.S. national phase application under 35 USC 371 of international application PCT/JP2019/025194, filed on Jun. 25, 2019, which claims priority to Japanese patent application No. 2018-124713, filed on Jun. 29, 2018. The entire disclosures of the above applications are incorporated herein by reference.

TECHNICAL FIELD

Embodiments of the present invention relate to an infectious disease prevention supporting device, method and program.

BACKGROUND ART

It is said that a person, as an adult, catches a cold about 2 to 5 times a year on average. The cause of a person catching a cold is a cold virus. It is difficult to take measures with vaccines against colds because there are at least 200 types of cold viruses, and therapeutics for acting on cold viruses have not yet been developed. It is therefore important to prevent the morbidity itself against colds.

Many of the cold viruses are known to enter the body from the mucosa, such as the nasal cavity of a person's face. Also, it has been confirmed that cold viruses enter the body through the lacrimal gland when a person touches his/her eye's mucosa.

It has been traditionally said that hand washing and gargling are effective in preventing a person from catching a cold. However, a cold virus may already have attached to an environmental surface that is routinely contacted by a person, such as a switch or a doorknob in a room.

Thus, even if, for example, a person washes his/her hands immediately after coming home from outside, if the person touches his/her mucosa with a hand that has touched the environmental surface described above, he/she may become infected with the cold virus. It has been therefore difficult for a person to sufficiently reduce the possibility of being infected with a cold virus by only hand washing or gargling.

Meanwhile, technologies for wearable devices such as smart watches have been developed. For example, an attempt has been made in which a wearable device is used for sensing a dietary habit of a person wearing the device (for example, see Non Patent Literature 1).

CITATION LIST

Non Patent Literature

Non Patent Literature 1: Shuzo, M., et al., "Wearable Eating Habit Sensing System Using Internal Body Sound", Journal of Advanced Mechanical Design, systems, and Manufacturing, Vol. 4, No. 1, 2010, pp. 158 to 166

SUMMARY OF THE INVENTION

Technical Problem

As described above, it is difficult to sufficiently reduce the possibility of catching a cold only by hand washing or the like. Here, even if the person tries to be careful not to unnecessarily touch his/her own mucosa with their hand, since such an action is unconsciously performed, it is difficult to suppress the action only by his/her own consciousness. Thus, in the current state, a person's action of touching his/her mucosa with their hand and causing a cold or other infectious disease cannot be appropriately suppressed.

Meanwhile, attempts have been made to sense various conditions, such as dietary habits, of a person by using a wearable device. However, currently, sensing a behavior causing a cold or other infectious disease has not been considered.

The present invention has been made in view of the above circumstances, and an object of the present invention is to provide an infectious disease prevention supporting device, method and program capable of appropriately supporting prevention of an infectious disease caused by viral entry into a person's mucosa.

Means for Solving the Problem

In order to achieve the above object, a first aspect of an infectious disease prevention supporting device according to one embodiment of the present invention is an infectious disease prevention supporting device including a processor, wherein the processor is configured to perform a detection process that detects a motion of a forearm or a wrist by a user, a proximity determination process that determines, based on the motion detected by the detection process for a predetermined period of time, whether the hand of the user is in proximity to a mucosa of a face of the user, and a warning generation process that generates, when it is determined by the proximity determination process that the hand of the user is in proximity to the mucosa, a warning to suppress the proximity.

A second aspect of the infectious disease prevention supporting device of the present invention is the infectious disease prevention supporting device according to the first aspect, wherein the processor is configured to further perform a direction determination process that determines, based on the motion detected by the detection process for a predetermined period of time, a direction of the motion of the forearm of the user, before the user brings the hand in proximity to the mucosa of the face, and to determine, in the proximity determination process, based on the motion detected by the detection process for the predetermined period of time, that the hand of the user is in proximity to the mucosa of the face when a direction of the motion of the forearm determined by the direction determination process is in a predetermined direction.

A third aspect of the infectious disease prevention supporting device of the present invention is the infectious disease prevention supporting device according to the first or second aspect, wherein the processor generates a warning to the user by a vibration, in the warning generation process, when it is determined by the proximity determination process that the hand of the user is in proximity to the mucosa.

A fourth aspect of the infectious disease prevention supporting device of the present invention is the infectious disease prevention supporting device according to the first or second aspect, wherein the processor generates a warning to the user by a visual means, in the warning generation process, when it is determined by the proximity determination process that the hand of the user is in proximity to the mucosa.

A fifth aspect of the infectious disease prevention supporting device of the present invention is the infectious disease prevention supporting device according to the first or second aspect, wherein the processor generates a warning to the user by an auditory means, in the warning generation process, when it is determined by the proximity determination process that the hand of the user is in proximity to the mucosa.

One aspect of a method of supporting prevention of an infectious disease according to one embodiment of the present invention is performed by a device including a processor, the method including detecting, by the processor, a motion of a forearm or a wrist by a user, determining, by the processor, whether the hand of the user is in proximity to a mucosa of a face of the user based on the motion detected for a predetermined period of time, and generating, by the processor, a warning to suppress the proximity when the processor determines that the hand of the user is in proximity to the mucosa.

One aspect of the infectious disease prevention support processing program according to one embodiment of the present invention causes the processor included in the infectious disease prevention supporting device according to any one of the first to fifth aspects to execute the processes performed by the infectious disease prevention supporting device.

Effects of the Invention

In a first aspect of the infectious disease prevention supporting device according to one embodiment of the present invention, a warning is generated to the user when the user brings the hand in proximity to the mucosa of the face. This can prevent a motion of the user's hand from causing an infectious disease.

In a second aspect of the infectious disease prevention supporting device according to one embodiment of the present invention, it is determined whether the user's hand is in proximity to the mucosa of the face considering a direction of a motion of the user's forearm at a timing before the user brings the hand in proximity to the mucosa of the face. This enables an appropriate determination of the user touching the mucosa of his/her face.

In a third aspect of the infectious disease prevention supporting device according to one embodiment of the present invention, a warning to the user is generated by a vibration when the proximity is determined. Thus, a warning can be reliably notified to, for example, a user with a visual or hearing disability to suppress the motion of his/her hand from causing an infectious disease.

In a fourth aspect of the infectious disease prevention supporting device according to one embodiment of the present invention, a warning to the user is generated by a visual means when the proximity is determined. Thus, a warning can be reliably notified to, for example, a user with a hearing disability to suppress the motion of his/her hand from causing an infectious disease.

In a fifth aspect of the infectious disease prevention supporting device according to one embodiment of the present invention, a warning to the user is generated by an auditory means when the proximity is determined. Thus, in a case where the user is in a dark location or when the user has a visual disability, a warning can be properly notified to the user to prevent the motion of the user's hand from causing an infectious disease.

That is, the present invention enables an appropriate support for the prevention of an infectious disease caused by viral entry into a person's mucosa.

DESCRIPTION OF EMBODIMENTS

Hereinafter, one embodiment of the present invention will be described below with reference to the drawings.

Overview of Embodiment

In one embodiment of the present invention, a cold prevention supporting device configured by installing a sensor and a vibrator in a wristwatch device that people (hereinafter, users) can wear in everyday life.

In the cold prevention supporting device, an acceleration of a forearm (which may hereinafter be referred to simply as an arm) or wrist (which may hereinafter be referred to as a "forearm or the like") when his/her hand is brought close to a mucosa of the eyes, nose, or mouth of his/her face or a periphery thereof is detected by a sensor. During this detection, a vibration is generated by activating the vibrator installed in the device. With this vibration, the cold prevention supporting device alerts to users. This prevents a habit of a person of touching a mucosa or its periphery, such as his/her nose or mouth.

However, assuming that a user is alerted by the vibrator only based on a detection result of an acceleration of a motion of the forearm or the like, for example, when the user brings his/her hand close to his/her eyes, nose, or the like, the following case would activate the vibrator to annoy the user. The case is, for example, an action taken during a meal when the user is not intending to touch a mucosa or the like of his/her eyes, nose, or the like.

Thus, in one embodiment of the present invention, the following will describe functions of the cold prevention supporting device distinguishing an action in which a user raises and brings his/her arm close to his/her face in order to pick up a dish or the like during a meal from an action in which the user raises and brings his/her arm close to his/her face to touch a mucosa or the like of his/her eyes, nose, or the like with his/her hand.

The user presses a notebook or a document with a light force or uses a keyboard of a personal computer (PC) when sitting at a desk for work or study, for example. Thus, the user's arm is directed in a pronation direction where the palm faces downward.

Meanwhile, the user usually holds a dish or the like by hand during a meal. Thus, the user's forearm or the like is directed rather in a supination direction (here, a direction in which the palm faces upward) as compared with the pronation direction, specifically, in an intermediate direction between pronation and supination.

When the user brings his/her hand close to the vicinity of his/her face during a meal, it is highly likely that the user is carrying food to the mouth. It is therefore desirable not to activate the vibrator. On the other hand, when the user brings his/her hand close to the vicinity of his/her face while working or studying, for example, it is highly likely that the user is intending to touch a mucosa or the like of his/her eyes or nose. It is therefore desirable to activate the vibrator in order to suppress the hand motion.

Thus, in one embodiment of the present invention, before detecting by the sensor an acceleration when the user brings his/her hand close to his/her eyes, nose, or the like, the cold prevention supporting device detects by the sensor and records the direction of the arm immediately before the detection of the acceleration.

Then, the cold prevention supporting device activates the vibrator when the sensor detects the acceleration of the hand brought in vicinity to the user's face and the sensor detects that the user's arm faces in the pronation direction or downward immediately before the detection of the acceleration. On the other hand, when the sensor detects that the user's arm is directed in another direction immediately before the above detection, the cold prevention supporting device does not activate the vibrator.

Thus, the cold prevention supporting device suppresses an operation of the vibrator when the user is not intending to touch a mucosa or the like of his/her eyes, nose, or the like.

That is, in one embodiment of the present invention, a cold prevention supporting device does not activate the vibrator when the user brings his/her hand close to his/her face with a cup, a bowl, or the like during a meal. On the other hand, when the user is intending to touch a mucosa or the like of the eyes, nose, or the like, the cold prevention supporting device activates the vibrator. This enables the cold prevention supporting device to break the user's bad habit and prevent a cold effectively.

One Embodiment of Present Invention

Hereinafter, the cold prevention supporting device according to one embodiment of the present invention will be described.

Here, a cold prevention supporting device that supports prevention of infection of a cold will be described. However, this device is not only used for colds but also used as an infectious disease prevention supporting device that supports prevention of other infectious diseases, such as influenza, which are caused by viral entry into the mucosa of a person's head. As described above, since there is currently no cold therapeutics, a cold prevention supporting device has a great advantage in preventing the morbidity of such infectious diseases.

Figure 1:
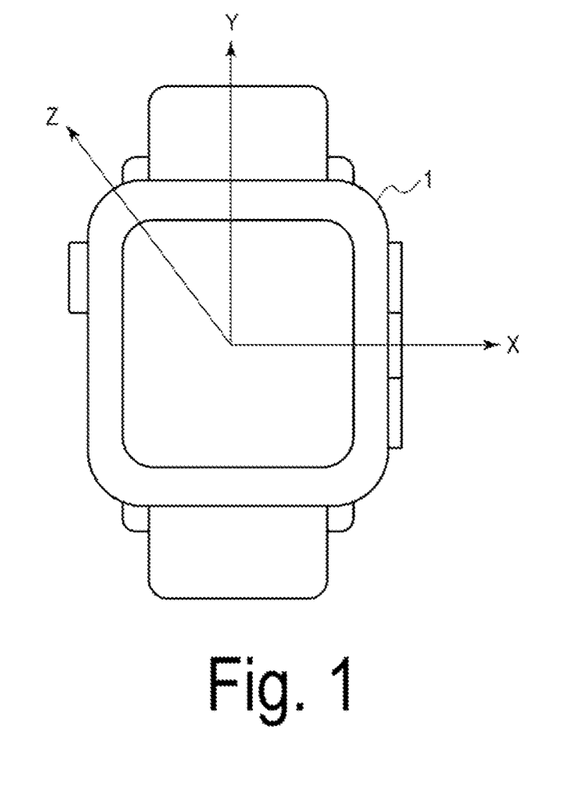
FIG. 1 is a diagram illustrating an example of a smart watch to which a cold prevention supporting device is applied according to one embodiment of the present invention.

FIG. 1 is a diagram illustrating an example of a smart watch to which the cold prevention supporting device is applied according to one embodiment of the present invention.

Figure 2:
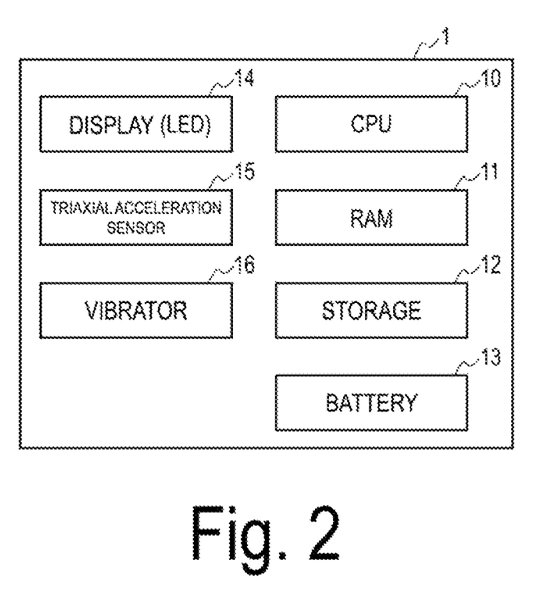
FIG. 2 is a block diagram illustrating a configuration example of the smart watch to which the cold prevention supporting device is applied according to one embodiment of the present invention.

FIG. 2 is a block diagram illustrating a configuration example of the smart watch to which the cold prevention supporting device is applied according to one embodiment of the present invention.

In one embodiment of the present invention, the cold prevention supporting device is achieved by a system using a computer device that is installed in a smart watch 1 worn by a user and is capable of executing programs.

In the example illustrated in FIG. 2, the smart watch 1 includes a central processing unit (CPU) 10 as an example of a general-purpose hardware processor, a random access memory (RAM) 11, a storage 12, a battery 13, a display 14, a triaxial acceleration sensor 15, and a vibrator 16. The CPU 10 is responsible for the overall processing operation of the smart watch 1.

The RAM 11 and the storage 12 are connected to the CPU 10. The RAM 11 is used as a working memory by the CPU 10. The RAM 11 includes a volatile memory such as synchronous dynamic random access memory (SDRAM). The storage 12 is configured by a storage device having a storage medium using a non-volatile memory capable of writing and reading at any time. The non-volatile memory is, for example, a hard disk drive (HDD) or a solid state drive (SSD). The storage 12 stores various programs including processing programs by the CPU 10, and various data in processing by the CPU 10.

Each program stored in the storage 12 includes a computer-executable instruction. The programs (computer-executable instructions), when executed by the CPU 10, cause the CPU 10 to perform a predetermined process. For example, the programs to implement functions of parts in the smart watch 1, when executed by the CPU 10, cause the CPU 10 to perform a series of processes described about each unit in the smart watch 1.

The battery 13 generates power to drive each unit in the smart watch 1. The display 14 may be achieved by, for example, a liquid crystal display (LED) or an electronic display.

The triaxial acceleration sensor 15 detects accelerations in X-axis direction (horizontal direction), Y-axis direction (horizontal direction and a direction orthogonal to the X-axis direction), and Z-axis direction (vertical direction) shown in FIG. 1. The arrow directions shown in FIG. 1 are positive axial directions. The vibrator 16 generates a vibration by vibrating a vibration mechanism (not illustrated) in the smart watch 1.

Figure 3:
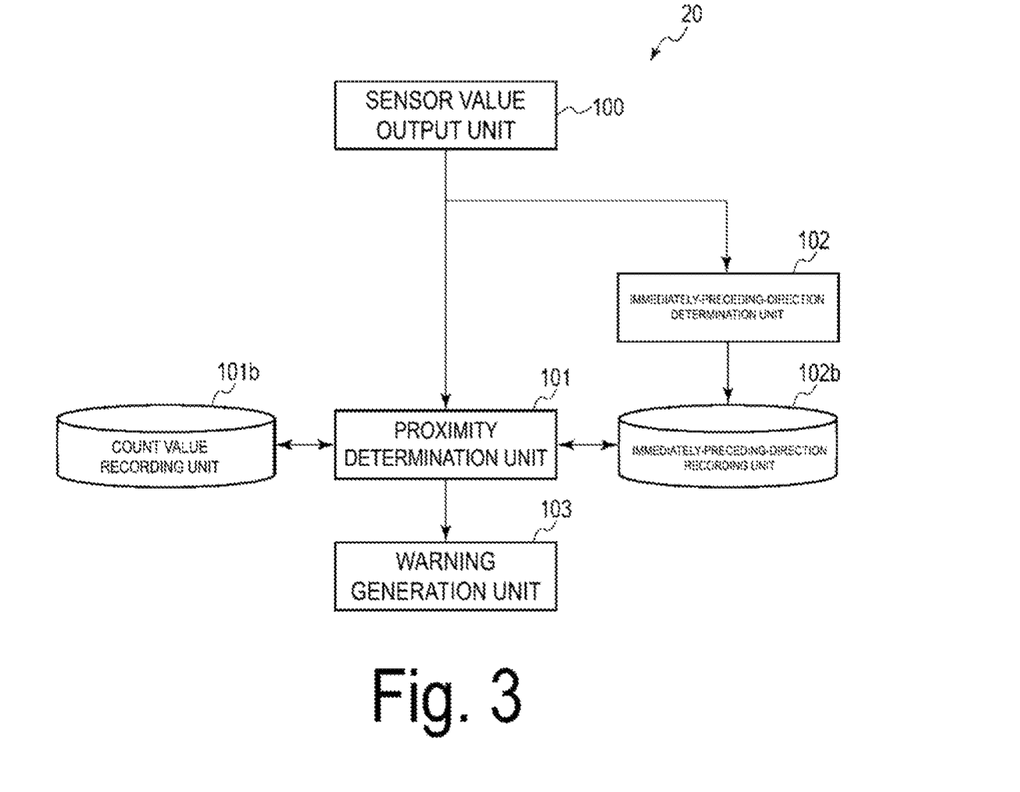
FIG. 3 is a functional block diagram illustrating the cold prevention supporting device according to one embodiment of the present invention.

FIG. 3 is a functional block diagram illustrating an example of the cold prevention supporting device 1 according to one embodiment of the present invention. As illustrated in FIG. 3, the cold prevention supporting device 20 achieved by the smart watch 1 includes a sensor value output unit 100, a proximity determination unit 101, a count value recording unit 101*b*, an immediately-preceding-direction determination unit 102, an immediately-preceding-direction recording unit 102*b*, and a warning generation unit 103. Details of each unit will be described below.

The functions of the sensor value output unit 100, the proximity determination unit 101, the immediately-preceding-direction determination unit 102, and the warning generation unit 103 are achieved by, for example, the CPU reading and executing the programs stored in the storage 12. Some or all of these functions may be achieved by a circuit such as an application specific integrated circuit (ASIC). The count value recording unit 101b and the immediately-preceding-direction recording unit 102b can be achieved, for example, by the RAM 11 or the storage 12 described above.

Figure 4:
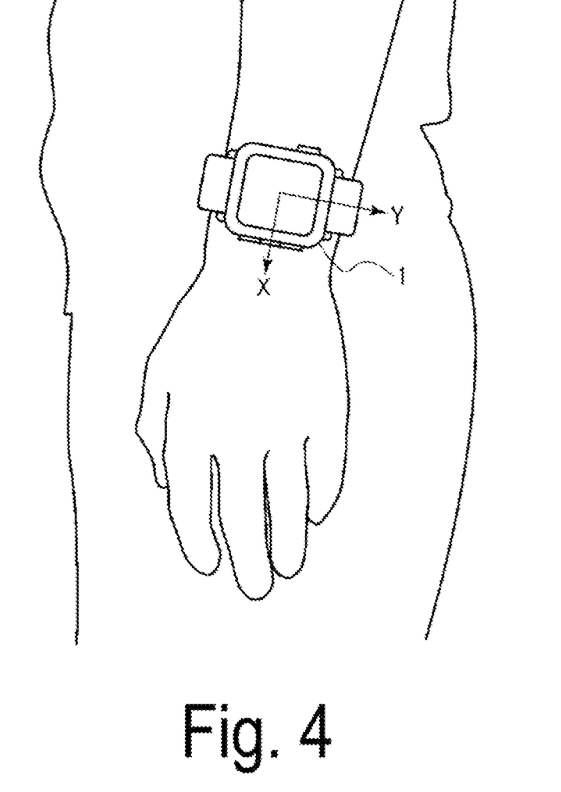
FIG. 4 is a diagram illustrating a first example of how the smart watch is worn.

FIG. 4 is a diagram illustrating a first example of how the smart watch is worn. In the example illustrated in FIG. 4, the user whose forearm and hand are kept downward is wearing the smart watch 1 such that the smart watch 1 is located in the vicinity of the wrist of the forearm of the left arm and such that a display surface of the display 14 is located on the side of the back of the hand.

In FIG. 4, an acceleration in XY-axis directions (X-axis direction and Y-axis direction) detected by the triaxial acceleration sensor 15 is shown when the user wearing the smart watch 1 leaves their forearm and hand downward. The Z-axis direction is omitted from the drawing.

That is, the triaxial acceleration sensor 15 can detect a motion of the user's forearm or wrist while the smart watch is worn in the vicinity of the user's wrist. The position at which the smart watch 1 is worn is not limited to the vicinity of the wrist as long as the acceleration representing the motion of the forearm or the like is detected correctly by the triaxial acceleration sensor 15.

The triaxial acceleration sensor 15 can acquire the sensor values of the acceleration in each axial direction at a sampling period of 10 Hz. However, when a program of the cold prevention supporting device 20 is activated for every sampling period, the power consumption of the battery 13 of the smart watch 1 has a great impact on normal use of the smart watch 1.

Thus, in one embodiment of the present invention, the sensor values acquired at the sampling period are temporarily stored in the RAM 11 or a buffer (not illustrated), and the program of the cold prevention supporting device 20 is called only at one sampling per 10 samplings, that is, every one second. This may reduce the power consumption of the battery 13 of the smart watch 1.

This program is a program that is driven by a so-called event and is activated only when the program is called. When the program is called, the sensor value output unit 100 collectively receives the sensor values in the X-axis direction, the Y-axis direction, and the Z-axis direction detected at 10 samplings from the RAM 11, and stores the sensor values, for example, in storage 12.

Figure 5:
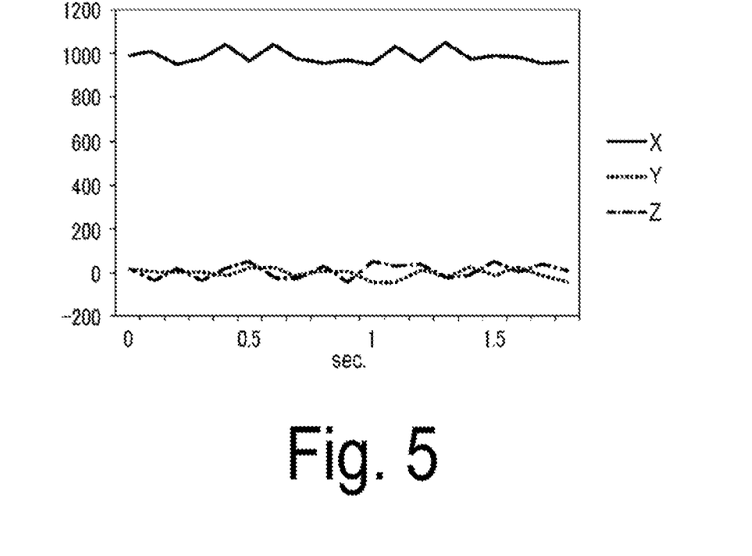
FIG. 5 is a diagram illustrating a first example of sensor values detected by a triaxial acceleration sensor.

FIG. 5 is a diagram illustrating a first example of sensor values detected by the triaxial acceleration sensor. FIG. 5 illustrates an example of sensor values in the directions including the XY-axis directions shown in FIG. 4. In the example shown in FIG. 5, when a gravitational acceleration is 1 G and the user leaves the forearm or the like downward, the sensor value in the X-axis direction is about "1,000". The sensor values described below are also values when a gravitational acceleration value is 1 G.

Here, when, for example, a sensor value equal to or greater than "650" in the X-axis direction is continuously detected, it is considered that the user leaves the forearm and the like substantially downward.

Figure 6:
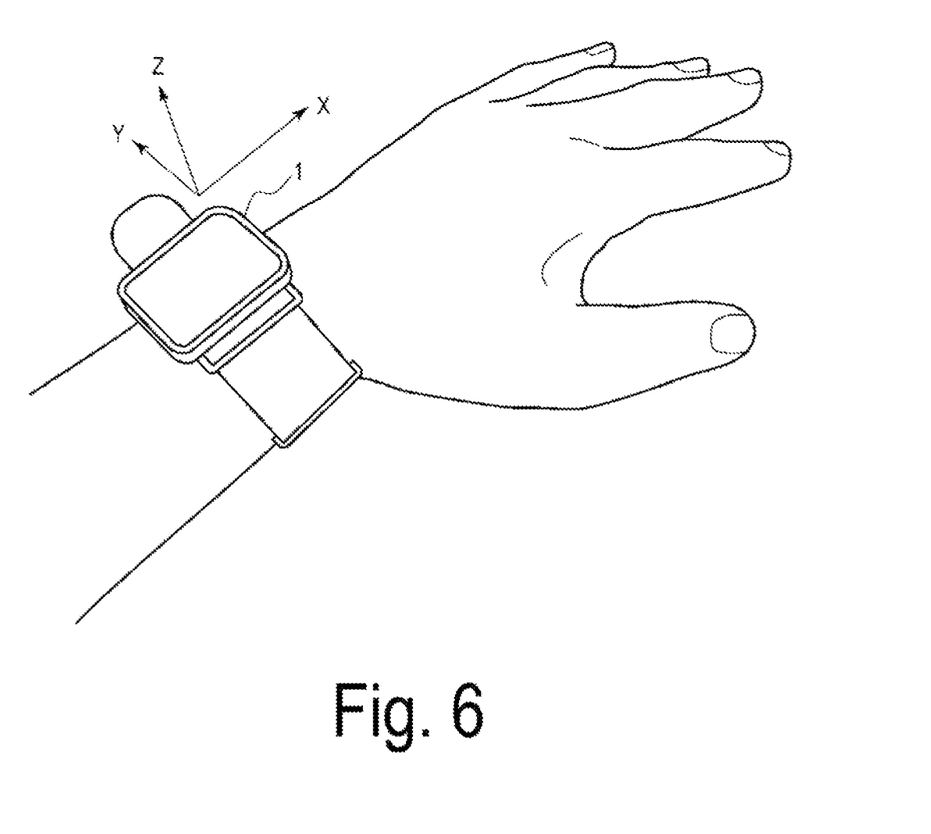
FIG. 6 is a diagram illustrating a second example of how the smart watch is worn.
Figure 7:
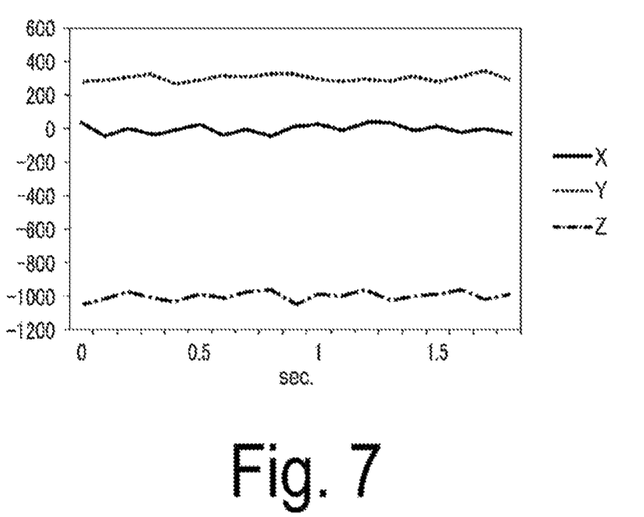
FIG. 7 is a diagram illustrating a second example of sensor values detected by the triaxial acceleration sensor.

FIG. 6 is a diagram illustrating a second example of how the smart watch is worn. FIG. 7 is a diagram illustrating a second example of sensor values detected by the triaxial acceleration sensor.

The example shown in FIG. 6 shows the accelerations in the XYZ-axis directions (X-axis direction, Y-axis direction, and Z-axis direction) detected by the triaxial acceleration sensor 15 of the smart watch 1 when the user places their forearm and hand directing in one direction on a desk. FIG. 7 illustrates an example of sensor values in the axis directions including the XYZ-axis directions illustrated in FIG. 6.

In the example shown in FIG. 7, when the user places their forearm and hand on a desk in a direction shown in FIG. 6, the sensor value in the Z-axis direction is about "−1000". Such a direction of the forearm and hand often occurs when the user is studying using a notebook or the like, or when the user is working using a PC keyboard.

Thus, for example, when sensor values of equal to or less than "−900" in the Z-axis direction are continuously detected, the cold prevention supporting device achieved by the smart watch 1 can determine that the user is at a desk with their forearm and hand turned in the pronation direction. Accordingly, the cold prevention supporting device can determine that the user is at the desk for a purpose other than a meal.

Figure 8:
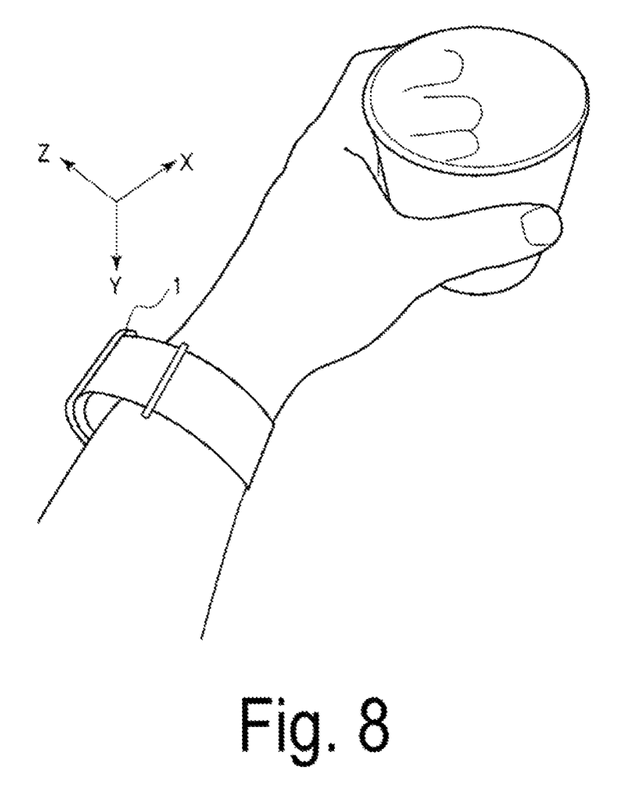
FIG. 8 is a diagram illustrating a third example of how the smart watch is worn.
Figure 9:
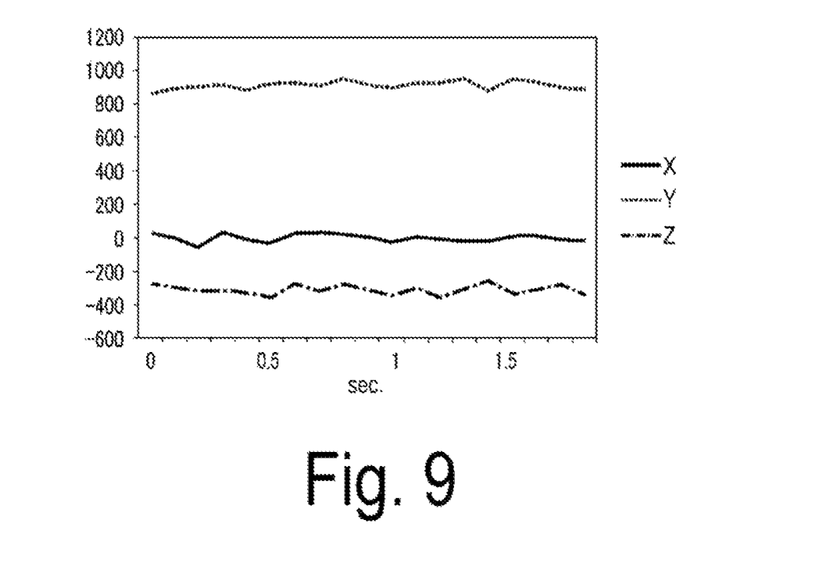
FIG. 9 is a diagram illustrating a third example of sensor values detected by the triaxial acceleration sensor.

FIG. 8 is a diagram illustrating a third example of how the smart watch is worn. FIG. 9 is a diagram illustrating a third example of sensor values detected by the triaxial acceleration sensor.

The example shown in FIG. 8 illustrates the acceleration of the smart watch 1 in the XYZ-axis directions detected by the triaxial acceleration sensor 15 of the smart watch 1 when the user places their forearm and hand on a table while holding a cup with their hand. FIG. 9 illustrates an example of sensor values in the axis directions including the XYZ-axis directions illustrated in FIG. 8.

In the example shown in FIG. 9, the sensor values in the Z-axis direction when the user is holding the cup by hand as shown in FIG. 8 are values (about −300) that is widely different from the sensor values (about −1,000) in the state shown in FIG. 7.

Figure 10:
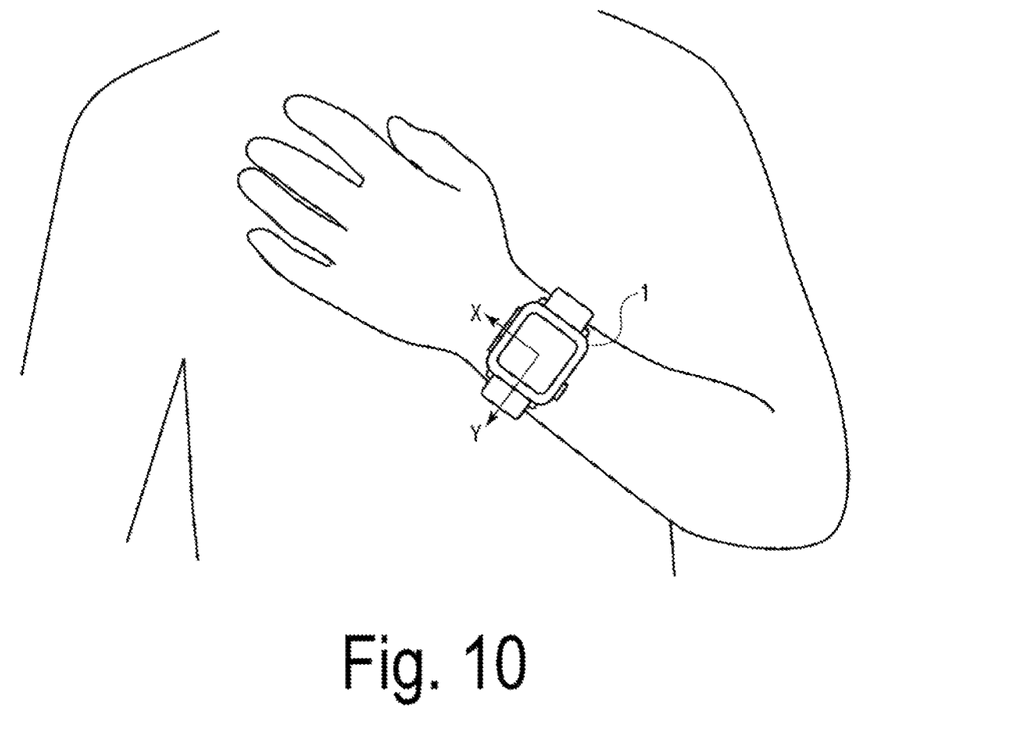
FIG. 10 is a diagram illustrating a fourth example of how the smart watch is worn.
Figure 11:
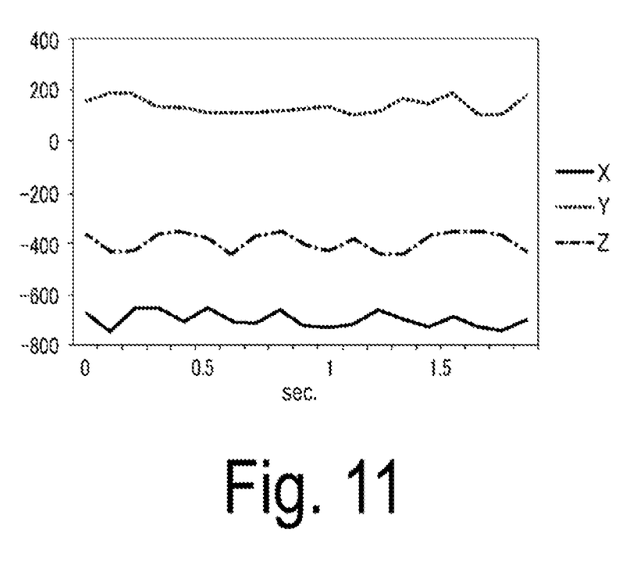
FIG. 11 is a diagram illustrating a fourth example of sensor values detected by the triaxial acceleration sensor.

FIG. 10 is a diagram illustrating a fourth example of how the smart watch is worn. FIG. 11 is a diagram illustrating a fourth example of sensor values detected by the triaxial acceleration sensor.

The example shown in FIG. 10 shows the acceleration in the XY-axis directions detected by the triaxial acceleration sensor 15 of the smart watch 1 when the user is intending to bring his/her hand close to the vicinity of his/her face. FIG. 11 illustrates an example of the sensor values in the XY-axis directions illustrated in FIG. 10.

In the example shown in FIG. 11, the sensor values in the X-axis directions are values of about "−700" when the user is intending to bring his/her hand close to the vicinity of his/her face.

Note that the sensor values in the Z-axis direction are values of about "−400" in FIG. 11. When the user is intending to bring his/her hand close to the vicinity of his/her face, the wrist may be rotated in the pronation direction. However, in this case, the sensor values in the Z-axis direction will be values having a different trend from the above values of about "−400".

Thus, in one embodiment of the present invention, for example, when the sensor values in the X-axis direction are continuously detected within a range of "−850" to "−650", the cold prevention supporting device in the smart watch 1 can determine that the user has brought his/her hand close to his/her face.

Figure 12:
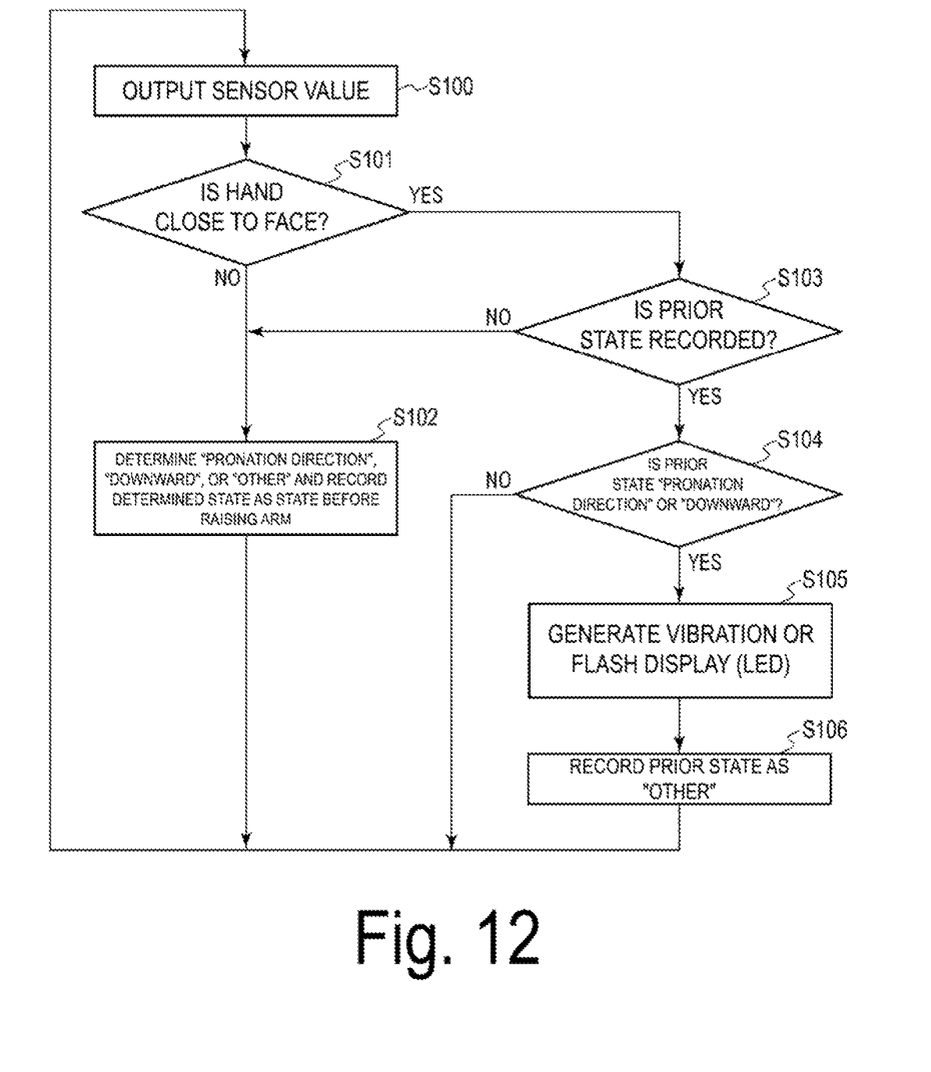
FIG. 12 is a flowchart illustrating an example of processing operation of the cold prevention supporting device according to one embodiment of the present invention.

FIG. 12 is a flowchart illustrating an example of processing operation of the cold prevention supporting device according to one embodiment of the present invention.

When the sensor values detected by 10 samplings, in the XYZ-axis directions, detected by the triaxial acceleration sensor 15 are accumulated in the RAM 11, for example, the sensor value output unit 100 outputs the sensor values to the proximity determination unit 101 and the immediately-preceding-direction determination unit 102 (S100).

By outputting the sensor values detected by a plurality of samplings collectively to the proximity determination unit 101 in this way, a frequency of determination by the proximity determination unit 101 can be reduced. Accordingly, the power consumption of the battery 13 of the smart watch 1 can be reduced. It is assumed that the output sensor values in the axis directions are output in chronological order, here as 10 arrays.

Next, the proximity determination unit 101 determines whether the user's hand is in proximity to the user's face (see FIGS. 10 and 11) (S101).

Here, when of the output 10 sensor values in the X-axis direction, the number of sensor values corresponding to continuous time for a predetermined period of time is within a specified range, the proximity determination unit 101 determines that the user's hand is in proximity to the user's face. Here, the predetermined period of time is set to 0.7 seconds, the number corresponding to the continuous time is seven, and the specified range is set to a range of, for example, "−850" or greater and "−650" or less.

As described above, the sensor values in the X-axis direction are output from the sensor value output unit 100 every 1 second as 10 arrays. Thus, a group of sensor values within the above specified range that are continuous for the above predetermined period of time (0.7 seconds) may span the previously output group of sensor values (here, a sensor value group of 10 sensor values) and the next output group of sensor values (here, a sensor value group of 10 sensor values) arranged in chronological order.

Here, it is assumed that the chronologically continuous 10 sensor values in the X-axis direction output at a single time do not satisfy a condition that continuous sensor values over the predetermined period of time (0.7 seconds), or here, seven or more chronologically continuous sensor values are within the specified range (range of "−850" to "−650").

In a case where the condition is not satisfied, when the end of the above 10 sensor values or the chronologically continuous sensor values including the end of the sensor values are within the specified range, the proximity determination unit 101 counts the number of the sensor values, for example, three, and this counted number will be held in the count value recording unit 101*b*.

Then, upon receiving a new chronologically continuous plurality of sensor values output from the sensor value output unit 100, the proximity determination unit 101 can count the beginning of these sensor values or the number of chronologically continuous sensor values within the specified range including the beginning of the sensor values together with the number of sensor values that have been held.

For example, it is assumed that the number of chronologically continuous sensor values in the X-axis direction within the specified range which acquired at the previous sampling period and held in the count value recording unit 101*b* is three as described above.

It is also assumed that the beginning of the new 10 chronologically continuous sensor values obtained at the next sampling period or the chronologically continuous sensor values in the X-axis direction including the beginning of the sensor values are within the specified range.

At this time, when the sum of the number of sensor values within the specified range (four, for example) acquired in the next sampling period and the number of sensor values held in the count value recording unit 101*b* is 7 or greater, the proximity determination unit 101 can determine that the following condition is satisfied. The condition is that the continuous sensor values in the X-axis direction for the predetermined period of time (0.7 seconds) are within the specified range ("−850" or greater and "−650" or less).

In a case where it is determined that the user has not brought his/her hand close to his/her face (NO in S101), the proximity determination unit 101 sends the result of this determination to the immediately-preceding-direction determination unit 102. In response to this result, the immediately-preceding-direction determination unit 102 determines a "state immediately before raising the arm" of the user (S102).

This determination result is utilized by the proximity determination unit 101 to determine whether the user has brought his/her hand close to the vicinity of his/her face based on the new sensor values obtained at the next sampling period. The above "state immediately before raising the arm" means the latest state of the direction of the motion of the forearm or the like before the user brings his/her hand close to the vicinity of his/her face.

Here, the immediately-preceding-direction determination unit 102 first determines whether the user's forearm or the like is facing downward, that is, whether the direction of the user's forearm or the like is vertically downward (hereinafter, also referred to as downward), based on whether the chronologically continuous sensor values in the X-axis direction are equal to or greater than a predetermined value (for example, 650 or greater) for a predetermined period of time (see FIGS. 4 and 5).

When it is determined that the user's forearm or the like faces downward, the immediately-preceding-direction determination unit 102 records data indicating that the "state immediately before raising the arm" is "downward" in the immediately-preceding-direction recording unit 102*b*.

Also, when it is not determined that the user's forearm or the like is facing downward, the user's forearm or the like should be directed in a direction above the vertically downward position.

Thus, the immediately-preceding-direction determination unit 102 determines whether the user's forearm or the like is facing in the pronation direction based on whether the sensor values in the Z-axis direction for a predetermined period of time satisfy a condition (for example, −900 or less) (see FIGS. 6 and 7).

When it is determined that the user's forearm or the like is facing in the pronation direction, the immediately-preceding-direction determination unit 102 records data indicating that the "state immediately before raising the arm" is the "pronation direction" in the immediately-preceding-direction recording unit 102*b*.

When it is not determined that the user's forearm or the like is facing in the pronation direction or downward, the immediately-preceding-direction determination unit 102 determines that the user's forearm or the like is facing in another direction, and records data indicating that the "state immediately before raising the arm" is "other" in the immediately-preceding-direction recording unit 102*b*.

After recording in the immediately-preceding-direction recording unit 102*b*, the processing returns to S100, and S101 is processed based on the new sensor values detected at the next sampling period.

Further, the processing when the proximity determination unit 101 determines that the user has brought his/her hand close to the vicinity of his/her face (YES in S101) and the data is stored in the immediately-preceding-direction recording unit 102*b* (YES in S103) will be described.

In this case, when the direction of the user's forearm or the like immediately before this determination recorded in the immediately-preceding-direction recording unit 102b is the "pronation direction" or "downward" (YES in S104), the proximity determination unit 101 determines that the user has brought his/her hand close to the vicinity of his/her face to touch the mucosa or the like of his/her eye, nose, or the like, and sends the result of this determination to the warning generation unit 103.

Note that, when the data is not recorded in the immediately-preceding-direction recording unit 102b (NO in S103) after "YES" is determined in S101, the processing proceeds to S102.

In response to the result of the determination that the user has brought his/her hand close to the vicinity of his/her face, the warning generation unit 103 activates the vibrator 16 to generate a vibration in order to suppress the proximity of his/her hand to his/her face (S105).

Alternatively, instead of activating the vibrator 16, the warning generation unit 103 may cause the display 14 to flash or otherwise signal sound output or the like by a speaker (not illustrated). Further, the warning generation unit 103 may cause the display 14 to display a message to indicate to the user that the user should not touch the mucosa or the like of his/her eyes, nose, or the like on the display 14, or output audio from the speaker to indicate to the user that the user should not touch the mucosa or the like of his/her eyes, nose, or the like.

Further, the warning generation unit 103 may generate a warning by a visual means other than the display 14 or by an auditory means other than the speaker.

As described above, the warning generation unit 103 may warn the user to suppress his/her proximity of his/her hand to his/her face.

Here, in a case where the user has a visual or hearing disability, for example, when a warning is generated to the user by a vibration, the warning can be reliably notified to the user to prevent a motion of the user's hand from causing infectious diseases.

Further, in a case where the user has a hearing disability, for example, when a warning is generated to the user by a visual means, the warning can be reliably notified to the user to prevent a motion of the user's hand from causing infectious diseases.

In a case where the user is in a dark location or the user has a visual disability, when a warning to the user is generated by an auditory means, a warning can be properly notified to the user to prevent the motion of the user's hand from causing infectious diseases.

Subsequently, the proximity determination unit 101 records the data indicating that the "state immediately before raising the arm" is "other" in the immediately-preceding-direction recording unit 102b (S106).

This data is referenced in the next determination in S101 by the proximity determination unit 101. After S106, the processing returns to S100. In S104, the processing is similar when it is determined that the direction of the user's forearm or hand is not the "pronation direction" or "downward" (NO in S104).

As explained above, in one embodiment of the present invention, when the user brings his/her hand close to his/her face, and the direction of the forearm or hand immediately before is in the pronation direction or downward, the infectious disease prevention supporting device determines that the user's hand has brought his/her hand to his/her face to touch the mucosa or the like of his/her eyes, nose, or the like, and generates a warning. Thus, the user can be properly warned for the prevention of a cold.

The present invention is not limited to the embodiments, and various modifications can be made without departing from the gist of the present invention in an implementing stage. Furthermore, the embodiments may be implemented in combination appropriately as long as it is possible, and in this case, combined effects can be obtained. Further, the above embodiments include inventions on various stages, and various inventions may be extracted by appropriate combinations of the disclosed multiple configuration requirements.

Further, a scheme described in each embodiment can be stored in a recording medium such as a magnetic disk (a Floppy (trade name) disk, a hard disk, or the like), an optical disc (a CD-ROM, a DVD, an MO, or the like), a semiconductor memory (a ROM, a RAM, a Flash memory, or the like) or transferred by a communication medium for distribution, as a program (a software unit) that can be executed by a computing machine (a computer). Note that the program stored on the medium side includes a setting program for configuring, in a computing device, a software means (including not only an execution program but also a table and a data structure) to be executed by the computing device. The computing device which achieves this device reads the program recorded in the recording medium, optionally builds the software means by the setting program, and executes the above-described processing by controlling the operation with the software means. Note that the recording medium referred to herein is not limited to a recording medium for distribution, but includes a storage medium such as a magnetic disk or a semiconductor memory provided in a computing machine or a device connected via a network.

REFERENCE SIGNS LIST

1 Smart watch
10 CPU
11 RAM
12 Storage
13 Battery
14 Display
15 Triaxial acceleration sensor
20 Cold prevention supporting device
100 Sensor value output unit
101 Proximity determination unit
101b Count value recording unit
102 Immediately-preceding-direction determination unit
102b Immediately-preceding-direction recording unit
103 Warning generation unit

The invention claimed is:

1. An infectious disease prevention supporting device comprising a processor,
wherein the processor is configured to perform:
a detection process that detects a motion of a forearm or a wrist by a user,
a direction determination process that determines, based on the motion detected by the detection process for a predetermined period of time, a direction of the motion of the forearm or the wrist of the user,
a first proximity determination process that determines, based on the motion detected by the detection process for a predetermined period of time, that the hand of the user is in proximity to the mucosa of the face of the user,
a second proximity determination process that determines that the hand of the user is in proximity to the mucosa of the face of the user with intent to touch the mucosa with the hand of the user when the direction of the forearm or the wrist determined by the direction determination process immediately before the first proximity determination process determines that the hand of the user is in proximity to the mucosa of the face of the user is in vertically downward or a pronation direction, and a warning generation process that generates, when it is determined by the proximity determination process that the hand of the user is in proximity to the mucosa, a warning to suppress the proximity.

2. The infectious disease prevention supporting device according to claim 1, wherein the processor is configured to generate a warning to the user by a vibration, in the warning generation process, when it is determined by the proximity determination process that the hand of the user is in proximity to the mucosa to touch the mucosa with the hand of the user.

3. The infectious disease prevention supporting device according to claim 1, wherein the processor is configured to generate a warning to the user by a visual means, in the warning generation process, when it is determined by the proximity determination process that the hand of the user is in proximity to the mucosa to touch the mucosa with the hand of the user.

4. The infectious disease prevention supporting device according to claim 1, wherein the processor is configured to generate a warning to the user by an auditory means, in the warning generation process, when it is determined by the proximity determination process that the hand of the user is in proximity to the mucosa to touch the mucosa with the hand of the user.

5. A method of supporting prevention of an infectious disease performed by a device including a processor, the method comprising:

detecting, by the processor, a motion of a forearm or a wrist by a user, determining, by the processor, based on the motion detected for a predetermined period of time, a direction of the motion of the forearm or the wrist of the user, before the user brings the hand of the user in proximity to a mucosa of a face of the user, first determining, by the processor, that the hand of the user is in proximity to the mucosa of the face of the user based on the motion detected for a predetermined period of time, second determining, by the processor, that the hand of the user is in proximity to the mucosa of the face of the user with intent to touch the mucosa with the hand of the user when the direction of the forearm or the wrist determined immediately before determining that the hand of the user is in proximity to the mucosa of the face of the user is in vertically downward or a pronation direction, and generating, by the processor, a warning to suppress the proximity when the processor determines that the hand of the user is in proximity to the mucosa.

6. The method according to claim 5, further comprising generating a warning to the user by a vibration when it is determined that the hand of the user is in proximity to the mucosa to touch the mucosa with the hand of the user.

7. The method according to claim 5 further comprising generating a warning to the user visually when it is determined by the proximity determination process that the hand of the user is in proximity to the mucosa to touch the mucosa with the hand of the user.

8. The method according to claim 5 further comprising generating a warning to the user audibly when it is determined by the proximity determination process that the hand of the user is in proximity to the mucosa to touch the mucosa with the hand of the user.

9. A non-transitory computer readable storage medium storing a program that causes the processor included in the infectious disease prevention supporting device to perform the processes performed by the infectious disease prevention supporting device according to claim 1.

* * * * *